United States Patent [19]

Preidel

[11] Patent Number: 5,376,244
[45] Date of Patent: Dec. 27, 1994

[54] ELECTROCHEMICAL DETERMINATION OF OXYGEN CONCENTRATION

[75] Inventor: Walter Preidel, Erlangen, Germany

[73] Assignee: Siemens Aktiengesellschaft, Munich, Germany

[21] Appl. No.: 941,132

[22] Filed: Oct. 29, 1992

[30] Foreign Application Priority Data

May 2, 1990 [DE] Germany ............................ 4014109

[51] Int. Cl.$^5$ ............................................ G01N 27/26
[52] U.S. Cl. ............................ 204/153.16; 204/153.17; 204/153.1
[58] Field of Search ............... 204/402, 153.16, 153.17, 204/153.1, 431, 432, 412

[56] References Cited

U.S. PATENT DOCUMENTS

| | | | |
|---|---|---|---|
| 2,913,386 | 11/1959 | Clark, Jr. ................. | 204/415 |
| 3,260,656 | 7/1966 | Ross, Jr. .................. | 204/415 |
| 4,076,596 | 2/1978 | Connery et al. .......... | 204/415 |
| 4,578,154 | 3/1986 | Kitamura et al. ........ | 204/153.17 |
| 4,853,091 | 8/1989 | Mund et al. .............. | 204/402 |
| 4,891,102 | 1/1990 | Albery et al. ............ | 204/153.17 |

Primary Examiner—John Niebling
Assistant Examiner—Bruce F. Bell
Attorney, Agent, or Firm—Kenyon & Kenyon

[57] ABSTRACT

In a process for electrochemically determining the oxygen concentration, in particular in body fluids, by means of an oxygen sensor having a sensor electrode, an exact oxygen determination is possible if a potential profile having a plurality of potential stages is impressed on the sensor electrode, the first potential stage being in the range between −0.5 and −1.2 V (1st measuring potential), the second potential stage being in the range between −0.5 and −1.3 V 2nd measuring potential) and the third potential stage being about 0 V, referred in all cases to an Ag/AgCl reference electrode, and there being between the two measuring potentials a potential difference of $\geq 50$ mV, the length of stay at the two measurement potentials is in each case between 10 and 50 ms (measurement period), the current flowing at the two measuring potentials is determined and is integrated with respect to time, the integration starting in each case about 5 to 30 ms after the start of the measurement period and lasting in each case between 5 and 10 ms, and the oxygen concentration is determined by taking the difference between the two integrals.

12 Claims, No Drawings

ELECTROCHEMICAL DETERMINATION OF OXYGEN CONCENTRATION

BACKGROUND OF THE INVENTION

The invention relates to a process for electrochemically determining the oxygen concentration, in particular in body fluids, by means of an oxygen sensor having a sensor electrode, and also to an oxygen sensor employing said process.

The measurement of oxygen concentration or of oxygen partial pressure is an important analytical problem. In medical technology, in particular, a rapid and accurate determination of the oxygen value is necessary. Thus, the determination of the oxygen in the blood of patients requires an accuracy of approximately 1 torr, in particular, in the range between 10 and 200 torr. At the same time, the drift in the signal in the course of three days, which essentially corresponds to the duration of measurement in the blood, should not exceed a value of 5 torr. The oxygen sensors hitherto used in medicine, however, fail to meet these requirements by far.

At present, use is generally made in medical technology of the Clark oxygen sensor (in this connection see U.S. Pat. Nos. 2,913,386, 3,260,656 and 4,076,596), which is based on the electrochemical principle. Although this sensor can be used in blood gas analyzers, it is not, however, suitable for determining the oxygen content of the blood since some important features of the sensor are an obstacle to an implantation or an operation in the body lasting a fairly long time. These include, in particular, a hydrophobic membrane, which is disposed in front of the measuring electrode. The properties of said membrane are in fact markedly altered by interactions in the body. In addition, the continuous and high oxygen consumption of the sensor results in a marked rejection reaction which further impedes the operation of the sensor.

Published European Patent Application 0 170 998 discloses a process for electrochemically determining the oxygen concentration, in particular, in biological material, by means of an oxygen sensor having a measuring electrode and a counterelectrode. In this process, two potentials are impressed cyclically on the measuring electrode, the first potential (measuring potential) being in the range between $-1.4$ and $-0.4$ V and the second potential (recovery potential) in the range between $-0.2$ and $+0.2$ V, referred in all cases to an Ag/AgCl reference electrode; in this connection, the length of stay at the measuring potential is small compared with the cycle time. The measuring signal evaluated in this process is the current flowing during the measurement period, in particular in the form of the charge. The known process is primarily used to measure relative variations in the oxygen concentration in order to match the frequency of a heart pacemaker to the patient's requirements.

SUMMARY OF THE INVENTION

The object of the invention is to provide a process which makes possible (by using a sensor having a sensor electrode) an exact oxygen determination, i.e. a determination with an accuracy of approximately 1 torr.

According to the invention, this is achieved by a process wherein a potential profile having a plurality of potential stages is impressed on the sensor electrode, the first potential stage being in the range between $-0.5$ and $-1.2$ V (1st measuring potential), the second potential stage being in the range between $-0.5$ and $-1.3$ V (2nd measuring potential) and the third potential stage being about 0 V, referred in all cases to an Ag/AgCl reference electrode, and there being a potential difference between the two measuring potentials of $\geq 50$ mV, wherein the length of stay at the two measuring potentials is in each case between 10 and 50 ms (measurement period), wherein the current flowing at the two measuring potentials is determined and integrated with respect to time, the integration starting in each case about 5 to 30 ms after the start of the measurement period and lasting in each case between 5 and 10 ms, and wherein the oxygen concentration is determined by taking the difference between the two integrals.

DETAILED DESCRIPTION OF THE INVENTION

In the process according to the invention, in which a potential profile comprising a plurality of potential stages is cyclically impressed on the sensor electrode and the current response is evaluated, the oxygen partial pressure can be measured with the required accuracy. In the simplest case, the potential profile in this pulse method comprises three potential stages, the current being measured during the first two potential stages and the integral being determined in each case with respect to a certain time. The difference between the two integrals is then a function of the oxygen concentration.

In the process according to the invention, the measured value is dependent on the blood flow only at very low flow velocities ($\approx 2$ cm/s). Said process is consequently eminently suitable for a system for monitoring the oxygen partial pressure in the blood; in addition, it can also be used to determine oxygen in tissue fluid. An advantage of this pulse method is, furthermore, the low oxygen consumption; body reactions are in fact consequently reduced to a minimum.

The process according to the invention, in which a multiple potential jump occurs, employs two measuring potentials. In this connection, one of these two measuring potentials is used to suppress effects which are independent of the oxygen concentration. As a result of taking the difference between an integral (with respect to the current) at a potential at which the oxygen reduction is less pronounced but the zero current is nevertheless present, for example at $-0.8$ V, and an integral (with respect to the current) at a potential with a normally pronounced oxygen reduction, for example at $-1.0$ V, the zero effect can in fact be suppressed. The advantage is that the measurement signal at an oxygen partial pressure of 0 torr is about 0 A s. The calibration is consequently simpler and more stable since even a drift in the measurement signal at the beginning of the sensor operation is reduced.

In the process according to the invention, the first measuring potential, i.e. the potential range of the first measuring pulse, is in the range between $-0.5$ and $-1.2$ V and advantageously in the range between $-0.75$ and $-1.15$ V; preferably, the first measuring potential is approximately $-0.8$ V. The second measuring potential, i.e. the potential range of the second measuring pulse, is in the range between $-0.5$ and $-1.3$ V and advantageously in the range between $-0.85$ and $-1.25$ V; preferably, the second measuring potential is approximately $-1.0$ V. The third potential stage, i.e. the potential stage after the two measuring potentials, is about 0 V (with a band width of approximately $\pm 200$ mV);

the length of stay at this potential stage is advantageously between 0.5 and 10 s. In this connection, the potential data refer in all cases to an Ag/AgCl reference electrode.

The length of stay at the two measuring potentials, i.e. the time duration of the measuring pulses, is in each case 10 to 50 ms; preferably, this time interval is in each case approximately 20 ms. The current is integrated in each case about 5 to 30 ms after the start of the measurement period, i.e. after the start of the measuring pulse, and lasts between 5 and 10 ms in each case. Preferably, the integration starts in each case approximately 15 ms after the start of the measuring pulse and takes place in a time interval of 5 ms.

Advantageously, in the process according to the invention, two further potential stages are impressed on the sensor electrode before the first measuring potential. In this connection, the first of these two potential stages is in the range between −0.5 and −1.5 V, advantageously in the range between −0.8 and −1.3 V, and preferably approximately −1.0 V; the second potential stage is about 0 V (with a band width of approximately ±200 mV). The length of stay at the first of these further potential stages, i.e. the pulse length, is advantageously 10 to 50 ms. The length of stay at the second additional potential stage, i.e. the time lead (prior to the first measuring potential), is advantageously 10 to 150 ms.

The potential jump prior to the measuring potentials is used in the process according to the invention to measure the flow velocity of the blood, i.e. of the electrolyte. As a result of a pulse at an interval defined in time prior to the measuring potentials, a reduction of oxygen occurs in fact at the sensor electrode and in its immediate vicinity; the measurement then yields a lower measurement signal than without this preliminary pulse. This reduction (of the measurement signal) is a measure of the extent to which the oxygen is transported in the electrolyte in the region in front of the electrode. If measurement is now carried out alternately with and without preliminary pulse, information is obtained both about the oxygen partial pressure and about the transport of oxygen to the electrode. This, however, represents information about the flow velocity.

Furthermore, in the process according to the invention, the capacitance of the sensor electrode can be determined prior to the oxygen measurement and, consequently, the measured integral, i.e. the oxygen value, can be referred to the particular electrode or its individual properties, area and activity. This makes it possible to use various electrodes (without special calibration) with one electronic system. With such a procedure, even a calibration in the blood or in an NaCl solution with fixed oxygen partial pressures may under some circumstances be unnecessary.

An oxygen sensor according to the invention, i.e. a device for performing the process according to the invention, has a sensor electrode, a counterelectrode and a reference electrode; at the same time, the sensor electrode is composed, at least at the surface, of electrocatalytically inactive carbon. In said oxygen sensor, means are furthermore provided for impressing the desired potential profile on the sensor electrode, determining and integrating the current and determining the oxygen concentration.

As material for the sensor electrode (or for its surface) use is advantageously made of an electrocatalytically inactive carbon from the group comprising glassy carbon, pyrographite, sputtered carbon, sputtered graphite and amorphous hydrogen-containing carbon (a-C:H); in this connection, glassy carbon is preferably used. The counterelectrode is advantageously composed of platinum or, alternatively, of titanium. The reference electrode is preferably an Ag/AgCl For monitoring patients and similar purposes, the oxygen sensor according to the invention is advantageously used in the form of a catheter sensor. Such a catheter sensor, which is used, in particular, for measuring oxygen in the blood, has the following three-electrode arrangement: the sensor electrode, i.e. the working or measuring electrode, forms the catheter tip, while the reference electrode and the counterelectrode are arranged on the catheter behind the working or measuring electrode, each at a distance from one another. In this connection, the distance between the sensor electrode and the reference electrode, which is insulated from it, is, for example, 1 to 3 mm, while the distance between the reference electrode and the counterelectrode is 2 to 5 mm. It is advantageous if the reference electrode and the counterelectrode are of sleeve-like construction.

For the catheter material itself, polyurethane and polyorganosiloxanes, i.e. silicones, in particular, are suitable. The catheter itself is manufactured, for example, by the casting or injection molding process, connection being made beforehand to the electrodes and a connecting plug, which is generally triple-pole, being concomitantly encapsulated. Advantageously, provision can furthermore be made for the temperature of the catheter to be measured in addition, which can be carried out using a thermistor; in this case, a five-pole plug is then used. In addition, a measurement of the pressure may be provided. For this purpose, a capillary is then furthermore disposed within the catheter.

The invention will be explained in still greater detail by reference to exemplary embodiments.

EXAMPLE

The length of a catheter sensor which is to be disposed in the bloodstream is, for example, 10 to 12 cm, and the diameter 0.50 to 0.75 mm. The sensor electrode, which is composed, for example, of glassy carbon, has an area of approximately 1 $mm^2$ and comprises a hemisphere and a cylindrical casing. The reference electrode, in particular an Ag/AgCl electrode, has an area of approximately 0.45 $mm^2$ and comprises a cylindrical casing (having a free length of 1 mm). The counterelectrode, which is preferably composed of platinum or titanium, has an area of approximately 1.1 $mm^2$ and comprises a cylindrical casing (having a free length of 2.5 mm). The insulation resistance between the electrodes is approximately $1 \cdot 10^9$ Ω; the lead resistance of the sensor electrode is below 10 Ω.

The drive circuit of the catheter sensor generally comprises a potentiostat, a voltage source and an integrating and computing unit. During operation, for example, the following values apply: input resistance of the reference electrode: $1 \cdot 10^9$ Ω; capacitance of the reference electrode input: 20 pF: maximum current via the counterelectrode: 10 mA. These values may, however, be adjusted to the particular conditions.

The limitation of the current rise and of the maximum current is adjustable. The voltage source supplies, for example, the following potential stages: −800 mV/20 ms, −1000 mV/20 ms, 0 mV/1960 ms; in this connection, the following applies: time resolution: 1 ms; voltage: 5 mV absolute, 1 mV reproducibly. The current is integrated in the first and second potential stage in a time interval of 15 to 20 ms in each case after the start of the pulse; in this connection, the current to be expected is about 10 to 200 μA.

The current is tapped off as a voltage drop across a resistor in the counterelectrode circuit using an instrument amplifier; the measurement of the output signal or the further processing is carried out in digital or analog form. In both stages, the measured charge is about 50 nA.s to 1 μA.s. The taking of the difference between the two charges yields a value which is a measure of the oxygen concentration. The following applies to the charge measurement accuracy: 0.2 nA.s; measurement range: 0 to 2000 nA.s.

The oxygen partial pressure ($pO_2$) is calculated from the charge (Q) in accordance with:

$pO_2 = A.Q + B$ (linear equation) or
$pO_2 = A.Q^2 + B.Q + C$ (parabola).

The coefficients A, B and C are determined by measuring the electrode capacitance at 1 kHz in blood at the start of the oxygen measurement, in combination with an in-vitro calibration after the manufacture of the electrode.

What is claimed is:

1. A process for electrochemically determining oxygen concentration in a fluid using an oxygen sensor having a sensor electrode, comprising the steps of:
   impressing a potential profile having a plurality of potential stages on the sensor electrode, a first potential stage being in a range between −0.5 and −1.2 V as a first measuring potential, a second potential stage being in a range between −0.5 and −1.3 V as a second measuring potential, and a third potential stage being about 0 V, referred in all cases to an Ag/AgCl reference electrode, and there being a potential difference between the first and second measuring potentials of ≧50 mV and a length of stay at the first and second measuring potentials being in each case between 10 and 50 ms as a measurement period,
   determining a current flowing at the first and second measuring potentials and integrating the current with respect to time to obtain two integrals, the integration starting in each case about 5 to 30 ms after the start of the measurement period and having a duration in each case between 5 and 10 ms, and
   determining an oxygen concentration by taking the difference between the two integrals obtained from the step of integrating.

2. The process according to claim 1 wherein the length of stay at the third potential stage is between 0.5 and 10 s.

3. The process according to claim 2 wherein the first measuring potential is in a range between −0.75 and −1.15 V or the second measuring potential is in a range between −0.85 and −1.25 V.

4. The process according to claim 3 wherein two additional potential stages are impressed on the sensor electrode prior to the first measuring potential, the first additional potential stage being in a range between −0.5 and −1.5 V and the second additional potential stage being about 0 V.

5. The process according to claim 4 wherein the length of stay at the first additional potential stage is between 10 and 50 ms or the length of stay at the second additional potential stage is between 10 and 150 ms.

6. The process according to claim 2 wherein two additional potential stages are impressed on the sensor electrode prior to the first measuring potential, the first additional potential stage being in a range between −0.5 and −1.5 V and the second additional potential stage being about 0 V.

7. The process according to claim 6 wherein the length of stay at the first additional potential stage is between 10 and 50 ms or the length of stay at the second additional potential stage is between 10 and 150 ms.

8. The process according to claim 1 wherein the first measuring potential is in a range between −0.75 and −1.15 V or the second measuring potential is in a range between −0.85 and −1.25 V.

9. The process according to claim 8 wherein two additional potential stages are impressed on the sensor electrode prior to the first measuring potential, the first additional potential stage being in a range between −0.5 and −1.5 V and the second additional potential stage being about 0 V.

10. The process according to claim 9 wherein the length of stay at the first additional potential stage is between 10 and 50 ms or the length of stay at the second additional potential stage is between 10 and 150 ms.

11. The process according to claim 1 wherein two additional potential stages are impressed on the sensor electrode prior to the first measuring potential, the first additional potential stage being in a range between −0.5 and −1.5 V and the second additional potential stage being about 0 V.

12. The process according to claim 11 wherein the length of stay at the first additional potential stage is between 10 and 50 ms or the length of stay at the second additional potential stage is between 10 and 150 ms.

* * * * *